United States Patent
Vann et al.

(10) Patent No.: US 7,361,309 B2
(45) Date of Patent: Apr. 22, 2008

(54) MATRIX STORAGE AND DISPENSING SYSTEM

(75) Inventors: Charles S. Vann, Fremont, CA (US); David M. Cox, Foster City, CA (US)

(73) Assignee: Applera Corporation, Foster City, CA (US)

(*) Notice: Subject to any disclaimer, the term of this patent is extended or adjusted under 35 U.S.C. 154(b) by 0 days.

(21) Appl. No.: 11/436,296

(22) Filed: May 18, 2006

(65) Prior Publication Data

US 2006/0210434 A1    Sep. 21, 2006

Related U.S. Application Data

(63) Continuation of application No. 09/955,554, filed on Sep. 18, 2001, now Pat. No. 7,101,510, which is a continuation of application No. 09/251,232, filed on Feb. 16, 1999, now Pat. No. 6,432,719.

(51) Int. Cl.
*B01L 3/00* (2006.01)

(52) U.S. Cl. .................. 422/99; 422/63; 422/65; 422/100; 422/102; 436/180; 222/402.1; 222/566

(58) Field of Classification Search .......... 422/99–102, 422/63–65; 221/95; 436/180; 435/288.4; 222/402.1, 566
See application file for complete search history.

(56) References Cited

U.S. PATENT DOCUMENTS

| | | |
|---|---|---|
| 3,568,735 A | 3/1971 | Lancaster |
| 3,843,053 A | 10/1974 | Thoden |
| 3,974,854 A | 8/1976 | Kurpanek |
| 4,101,284 A * | 7/1978 | Difiglio et al. ............. 422/100 |
| 4,272,510 A | 6/1981 | Smith et al. |
| 4,415,098 A | 11/1983 | Haas |
| 4,444,336 A | 4/1984 | Nielsen |
| 4,559,201 A | 12/1985 | Yamada et al. |
| 4,593,728 A | 6/1986 | Whitehead et al. |
| 4,605,408 A | 8/1986 | Carpentier |
| 4,648,529 A | 3/1987 | Blakemore et al. |

(Continued)

FOREIGN PATENT DOCUMENTS

EP    0475533    3/1992

(Continued)

OTHER PUBLICATIONS

Brussolo, J.S. et al., "Automated Sample Handling Systems", NetSci Articles, vol. 1, No. 5, pp. 1-10, 1995.

(Continued)

*Primary Examiner*—Jill Warden
*Assistant Examiner*—Jyoti Nagpaul
(74) *Attorney, Agent, or Firm*—Kilyk & Bowersox P.L.L.C.

(57) ABSTRACT

The present invention provides a system and process providing variable access to, as well as quick and accurate dispensing of, numerous selected reagents from a mass storage arrangement. According to one embodiment, an array of reagent dispensers is supported over a movable platform assembly. The platform assembly aligns a designated receiving receptacle under a selected dispenser of the array so that a respective reagent can be dispensed therein. Advantageously, the apparatus and process can be carried out under the control of a programmed computer.

21 Claims, 8 Drawing Sheets

U.S. PATENT DOCUMENTS

| | | |
|---|---|---|
| 4,649,116 A | 3/1987 | Daty et al. |
| 4,681,742 A | 7/1987 | Johnson et al. |
| 4,699,884 A | 10/1987 | Noss et al. |
| 4,901,221 A | 2/1990 | Kodosky et al. |
| 4,914,568 A | 4/1990 | Kodosky et al. |
| 4,937,048 A | 6/1990 | Sakai et al. |
| 4,952,518 A | 8/1990 | Johnson et al. |
| 4,979,955 A | 12/1990 | Smith |
| 4,991,628 A | 2/1991 | Makela et al. |
| 5,011,779 A | 4/1991 | Maimon |
| 5,046,539 A | 9/1991 | MacLeish et al. |
| 5,135,695 A * | 8/1992 | Marcus ................ 264/141 |
| 5,291,587 A | 3/1994 | Kodosky et al. |
| 5,301,301 A | 4/1994 | Kodosky et al. |
| 5,301,336 A | 4/1994 | Kodosky et al. |
| 5,306,510 A | 4/1994 | Meltzer et al. |
| 5,382,512 A * | 1/1995 | Smethers et al. ............ 435/6 |
| 5,445,934 A | 8/1995 | Fodor et al. |
| 5,508,200 A | 4/1996 | Tiffany et al. |
| 5,525,302 A | 6/1996 | Astle |
| 5,571,258 A | 11/1996 | Pearson |
| 5,616,299 A | 4/1997 | Walker et al. |
| 5,620,853 A | 4/1997 | Smethers et al. |
| 5,649,576 A | 7/1997 | Kirk et al. |
| 5,677,195 A | 10/1997 | Winkler et al. |
| 5,685,459 A | 11/1997 | Wardle |
| 5,722,470 A | 3/1998 | Kedar et al. |
| 5,770,860 A | 6/1998 | Franzen |
| 5,773,296 A | 6/1998 | Montalbano et al. |
| 5,788,814 A | 8/1998 | Sun et al. |
| 5,798,035 A | 8/1998 | Kirk et al. |
| 5,812,410 A | 9/1998 | Lion et al. |
| 5,846,595 A | 12/1998 | Sun et al. |
| 5,935,859 A | 8/1999 | Elliott et al. |
| 5,979,251 A | 11/1999 | James et al. |
| 6,012,894 A | 1/2000 | Watanabe et al. |
| 6,074,609 A | 6/2000 | Gavin et al. |
| 6,117,391 A | 9/2000 | Mootz et al. |
| 6,136,274 A | 10/2000 | Nova et al. |
| 6,253,118 B1 | 6/2001 | Koyama |
| 6,432,719 B1 * | 8/2002 | Vann et al. .............. 436/180 |
| 7,101,510 B2 * | 9/2006 | Vann et al. ................ 422/99 |

FOREIGN PATENT DOCUMENTS

| | | |
|---|---|---|
| EP | 0803452 | 10/1997 |
| GB | 2099803 | 12/1982 |
| WO | WO 95/06253 | 3/1995 |
| WO | WO 95/30139 | 11/1995 |
| WO | WO 95/35505 | 12/1995 |
| WO | WO 96/36436 | 11/1996 |
| WO | WO 97/40383 | 10/1997 |
| WO | WO 97/44134 | 11/1997 |
| WO | WO 98/08092 | 2/1998 |
| WO | WO 98/15825 | 4/1998 |
| WO | WO 98/17383 | 4/1998 |
| WO | WO 98/38122 | 9/1998 |
| WO | WO 98/40159 | 9/1998 |

OTHER PUBLICATIONS

Castellino, A.M., "When the Chips are Down", Genome Research, vol. 7, pp. 943-946, 1997.

Editorial, "Getting Hip to the Chip", Nature Genetics, vol. 18, No. 3, pp. 195-197, 1998.

Fodor, S.P.A., et al., "Light-directed Spatially Addressable Parallel Chemical Synthesis", Science, vol. 251, pp. 767-773, 1993.

Haystack™ brochure, The Automation Partnership, First Edition: Oct. 1995.

International Search Report dated Sep. 25, 2000 from PCT/US00/03841.

Lemmo, A.V. et al., "Characterization of an Inkjet Chemical Mecrodispenser for Combinatorial Library Synthesis", Analytical Chemistry, vol. 69, No. 4, pp. 543-551, 1997.

* cited by examiner

MATRIX STORAGE AND DISPENSING SYSTEM

CROSS-REFERENCE TO RELATED APPLICATIONS

This application is a continuation of U.S. patent application Ser. No. 09/955,554, filed Sep. 18, 2001, now U.S. Pat. No. 7,101,510, which in turn is a continuation of U.S. patent application Ser. No. 09/251,232, filed Feb. 16, 1999, now U.S. Pat. No. 6,432,719. The complete disclosures of the above referenced patent applications are incorporated herein by reference in their entirities.

FIELD OF THE INVENTION

The present invention relates to the storage and dispensing of substances. More particularly, the invention provides a system, and method of use, for serially dispensing a large number of reagents into a plurality of receptacles.

BACKGROUND OF THE INVENTION

In chemical and biological laboratories, reagent transfer from a source vessel to a target receptacle is a fundamental task. Typically, a technician must retrieve various reagent bottles from a storage location, each containing a substance pertinent to the task at hand. The technician then manually pipettes a precise quantity of each into an appropriate reaction receptacle, such as a selected well of a multi-well plate. To prevent contamination, the pipette tip must be cleaned after contact with each different reagent, or it must be discarded and replaced with a new tip.

Alternatively, the technician can attempt to manually pour each of the collected reagents from its storage vessel into a desired reaction receptacle. However, given the ultra-small quantities of reagents typically called for in modern-day protocols, particularly for expensive reagents, this technique can be very tedious and difficult to accurately perform. Moreover, the act of pouring often leads to wasted reagent, e.g., where excessive amounts are inadvertently dispensed, and cross-contamination between receptacles can result, especially when working in a high-density receptacle format (e.g., a plate or tray having ninety-six wells).

Thus, it is not surprising that such manual techniques fail to meet the demands of most laboratories, where very small quantities of numerous (e.g., hundreds or thousands) reagents must be dispensed in a quick and accurate manner.

While systems are known that automate certain aspects of reagent storage, retrieval and/or dispensing, these too are associated with certain disadvantages. One such system, available from Sagian Inc. (Indianapolis, Ind.), automates the picking and placing of reagents. Briefly, to "pick" a reagent is to retrieve it from a reagent file, and to "place" it is to re-file it back into the reagent file. The Sagian system employs two industrial robots to move reagents to and from an operator area. The first robot is a mini-trieve that moves to a vertical file holding a target reagent and then pulls out an appropriate drawer containing the reagent. The robot then delivers the drawer to another work area where a CRS articulated robot removes the requested reagent, verifies that it is the correct container by passing the container in front of a bar-code scanner, and places it into one of a series of racks which are accessible by the operator. The mini-trieve then returns the drawer to its original location in the file. While eliminating much of the labor burden and handling errors generally associated with manual techniques, manual intervention is nevertheless required in order to dispense the reagent. Moreover, much wasted effort is involved since each drawer retrieved by the robot usually contains hundreds of additional reagents that do not pertain to the task at hand. Further, the robotic motions involved, and distances traversed, in retrieving each reagent can be quite substantial. Cumulatively, the overall process can be quite time consuming, particularly in situations where a great number of reagents (e.g., hundreds or thousands) must be retrieved.

Another automated system is sold under the trade name HAYSTACK, available from The Automation Partnership Group plc (Melbourn Science Park, Melbourn, Royston, Hertfordshire, UK). Similar to the Sagian system, the HAYSTACK system utilizes industrial robots to retrieve drawers of reagents from vertical files. In addition to such pick-and-place functions, The Automation Partnership offers modules that are able to carry out various dispensing steps. Such added capability, however, substantially increases the operational complexity of the system, and can consume a great deal of valuable laboratory space, as well.

There is, thus, a need for a relatively simple and compact reagent storage and dispensing system that provides for variable (custom) retrieval, as well as quick and accurate dispensing, of numerous selected reagents.

SUMMARY OF THE INVENTION

In one of its aspects, the present invention provides a system for storing and dispensing a plurality of reagents.

According to one embodiment, the system includes an addressable array of reagent dispensers, each having a gate mechanism disposed at a lower outlet region thereof. The gate mechanisms are independently operable between (i) an opened condition permitting passage of a respective reagent through the outlet region, and (ii) a closed condition whereat such passage is blocked. A first support is disposed below the dispenser array, and a second support, having a holding area for receiving a plurality of receptacles, is mounted on the first support. The first and second supports can be, for example, independently operable xy stages. The first support is variably positionable in a manner permitting placement of a fixed target region thereof directly under any selected one of the dispensers in the array. The second support is variably positionable in a fashion permitting placement of any selected target site of the receptacle-holding area directly over the fixed target region.

Each of the dispensers can be, for example, an elongated container having a longitudinally extending passageway configured to receive and hold a respective reagent when the gate mechanism is in the closed condition.

A rack having an array of holding cells can support the containers. According to one embodiment, the rack has at least 100 holding cells, and preferably in excess of 1,000 holding cells. Exemplary racks include, for example, 5,000, 10,000, 50,000, 100,000 and 500,000 holding cells. Each holding cell can be configured to removably support one of the containers in a substantially upright fashion. The holding cells can be configured to hold the containers at an average density, for example, of between about 2-8 containers per $cm^2$, or higher. In one embodiment, the containers are disposed in the rack at an average density of between about 3-6 containers per $cm^2$; and preferably between about 4-5 containers per $cm^2$. Multiple racks (e.g., 2, 3, 4, 5, or more) can be arranged in tandem for use in an "assembly line" type fashion.

A plurality of different reagents can be disposed in the dispensers. In one embodiment, each dispenser contains a reagent that is unique to the array.

Beads can be employed to carry the different reagents. One embodiment of the invention provides a plurality of bead groups, or "lots," with each lot being comprised of substantially similar beads carrying a respective one of the different reagents. The beads can be relatively large, e.g., about 1-5 mm in diameter; or the beads can be relatively small, e.g., each having a diameter of less than about a millimeter. In one preferred embodiment, each bead has a diameter of between about 275-325 µm; and preferably about 300 µm.

In one embodiment, a plurality of reagent-carrying beads are held in sealed ampules. In an exemplary arrangement, the ampules are dimensioned to move downward through a dispenser passageway under the force of gravity, in a substantially single-file fashion. Preferably, all of the beads in any given ampule carry the same, or a substantially similar, kind of reagent. Further in this embodiment, each passageway of the dispenser array is loaded with a plurality of such ampules.

One embodiment of the invention provides a detection assembly adapted to detect the passage of reagent dispensed from any one of the dispensers in the array. To this end, the detection assembly is provided with a field of view extending between the dispenser outlet regions and the second support.

According to one particular embodiment, the detection assembly includes a radiation emitter, such as a diode laser, and a radiation sensor. In an exemplary arrangement, the radiation emitter is (a) mounted on the first support at a region along one side of the second support, and (b) configured to project a substantially linear radiation beam along a pathway that passes over the fixed target region of the first support. The radiation sensor can be (a) mounted on the first support at a region along an opposing side of the second support, and (b) disposed within the radiation-beam pathway.

In one embodiment, each gate mechanism of the array is subject to a biasing force that normally urges it to the closed position, thereby preventing the passage of reagent through a respective outlet region. A release mechanism, adapted for positioning near any one of the gate mechanisms, is operable to apply a secondary force of a magnitude and direction effective to override the normal biasing force so that the gate mechanism assumes the opened condition.

In one particular embodiment, each gate mechanism includes a magnetic pinch valve having first and second permanent magnets that are pivotally mounted in facing relation at a respective outlet region. The magnets have lower, confronting north and south pole regions, respectively, that are normally urged toward one another by magnetic forces so as to pivot the magnets to the closed condition. Further in this embodiment, the release mechanism can be an electromagnet operable to generate a magnetic force having south and north pole portions disposed to attract the north and south pole lower regions of the first and second pivotal magnets, respectively, so that they swing away from one another (i.e., to an open condition).

In another particular embodiment, each gate mechanism is a resiliently deflectable lever having a protrusion normally extending into a respective outlet region. Further in this embodiment, the release mechanism is a rod adapted for reciprocal linear motion between a retracted position and an extended position. Upon movement toward the extended position, the rod can mechanically engage and deflect the lever, so that the protrusion is at least partially withdrawn from the outlet region (i.e., to an open condition).

The system of the invention can further include a guide or funnel member located over the fixed target region of the first support, between the dispenser array and the second support. In a preferred embodiment, the guide member is disposed for movement with the first support to a position under any selected dispenser. The guide member is configured to channel reagent dispensed from such dispenser to a selected site on the holding area of the second support.

In one particular embodiment, the guide member includes (i) an upper opening, or inlet, that is alignable with any one of the outlet regions for receiving reagent dispensed therefrom, and (ii) a lower opening, or outlet, through which dispensed reagent may egress in route to the holding area. Preferably, the upper opening is larger than the lower opening. A conical portion can be provided between the upper and lower openings.

In another of its aspects, the present invention provides a reagent dispenser assembly.

According to one preferred embodiment, the reagent dispenser assembly includes a container adapted to receive a reagent and a gate mechanism located at a lower outlet region of the container. The gate mechanism is provided with first and second permanent magnets pivotally mounted in facing relation at the lower outlet region. The pivotal magnets have lower, confronting north and south pole regions, respectively, that are normally urged toward one another by magnetic forces so as to swing them to a closed condition whereat the egression of reagent from the container is substantially blocked.

In one embodiment, an electromagnet is disposed below the gate mechanism. In this embodiment, the electromagnet is operable to generate a magnetic force having south and north pole portions disposed to attract the north and south pole lower regions of the first and second magnets, respectively, so that these regions swing away from one another to an opened condition. In this opened condition, the egression of reagent from the container is permitted.

Another embodiment provides a rack holding a plurality of the containers at respective locations defining an array. A first movable support is disposed below the rack, upon which the electromagnetic can be mounted.

A second movable support can be mounted on the first movable support, under the electromagnet. In this embodiment, the second movable support is configured to receive and hold a multi-well plate for receiving reagents dispensed from the containers.

Still a further aspect of the present invention provides a method for loading a plurality of receptacles with one or more reagents.

According to one embodiment, the method includes the steps of (i) placing the receptacles on a support under an addressable array of reagent dispensers;

(ii) selecting a dispenser equipped to dispense a desired reagent, and a receptacle for receiving the desired reagent;

(iii) simultaneously (a) positioning a fixed target region of the support at a location under the selected dispenser, and (b) positioning the selected receptacle at a location directly over the fixed target region of the support;

(iv) dispensing the desired reagent from the selected dispenser into the selected receptacle;

(v) detecting the desired reagent as it is dispensed from the selected dispenser; and (vi) repeating steps (ii)-(v) so that reagent is dispensed from at least one other dispenser into at least one other receptacle.

In one embodiment, each of the receptacles is a well of a multi-well tray.

In another embodiment, each of the dispensers is equipped to dispense an analyte-specific reagent that is unique to the array.

In a further embodiment, at least 100 different analyte-specific reagents are dispensed from respective dispensers into respective receptacles. Other embodiments contemplate the dispensing of at least 500, 1,000, and 10,000, different reagents.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which.

DETAILED DESCRIPTION OF THE INVENTION

Figure 1:
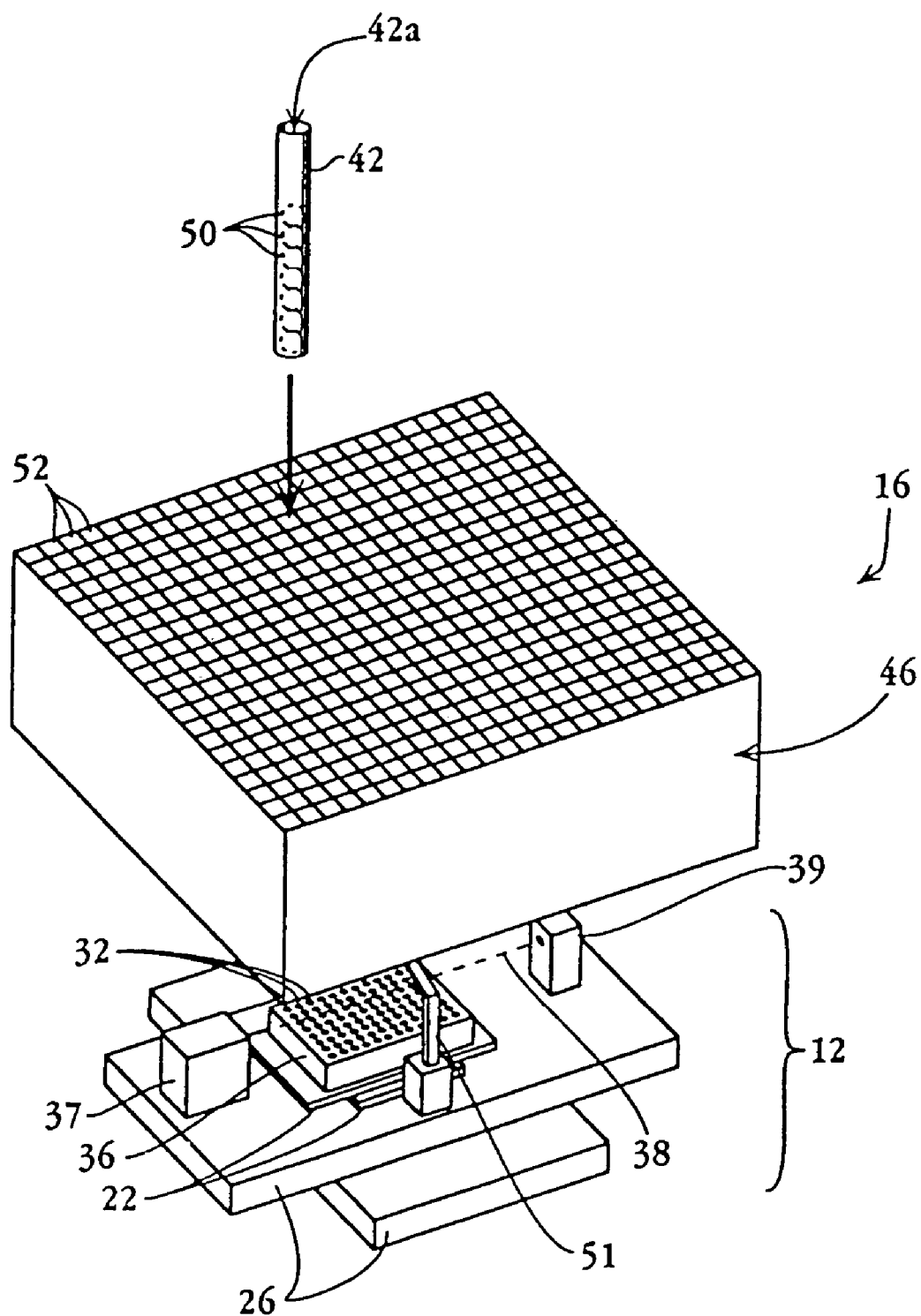
FIG. 1 is a perspective view of a reagent storage and dispensing system, showing a dispenser poised for insertion into a holding cell of a support rack, according to an embodiment of the present invention.

The following discussion of the preferred embodiments of the present invention is merely exemplary in nature. Accordingly, this discussion is in no way intended to limit the scope of the invention.

One aspect of the invention provides a system for dispensing a plurality of reagents. With initial reference to the embodiment of FIGS. 1-3, the system generally includes a movable table or platform assembly, denoted as 12, disposed under an addressable array of reagent dispensers, as at 16, equipped to serially dispense a plurality of reagents. As used herein, the wording "addressable array" refers to an array having a known reagent associated with a known location (address) in the array.

Platform assembly 12 includes an upper support 22 mounted on a lower support 26. Lower support 26 is movable such that a fixed (i.e., constant) target or reference region thereof, e.g., as indicated at 26a in the exploded view of FIG. 3, can be positioned below any selected dispenser of array 16. Upper support 22 is movable such that any selected (i.e., variable) target site of a receptacle-holding area thereof, visible as stippled region 22a in the embodiment of FIG. 3, can be positioned over the fixed target region of lower support 26.

Briefly, in operation, the fixed target region of the lower support is positioned under a dispenser holding a desired reagent. At the same time, a selected target site of the upper support's receptacle-holding area is positioned over the lower support's fixed target region. Typically, a particular receptacle held in a specific place on the receptacle-holding area, such as a well of multi-well plate 36, will be situated over the selected target site. Dispensed reagent, then, will fall toward the selected target site, landing in the receptacle. This procedure can be repeated to load other selected receptacles with desired reagents.

More particularly, the upper and lower supports, which can be xy positioners, e.g., stages, tables or similar devices, are adapted for variable positioning along respective, generally horizontal planes. Such positioning can be effected using automated means, e.g., motorized assemblies, or it can be manually effected. In one preferred embodiment, each of two xy stages is disposed in mechanical communication with a respective computer-controlled stepper motor (not shown) via a respective screw arrangement. Suitable xy stages and controllers are available commercially, for example, from NSK Inc. of Japan.

A control computer (not shown) integrates the operation of the stages, for example through a program written in an event driven language such as LABVIEW® or LABWIN-DOWS® (National Instruments Corp., Austin, Tex.). In particular, the LABVIEW software provides a high level graphical programming environment for controlling instruments. U.S. Pat. Nos. 4,901,221; 4,914,568; 5,291,587; 5,301,301; 5,301,336; and 5,481,741 (each expressly incorporated herein by reference) disclose various aspects of the LABVIEW graphical programming and development system. The graphical programming environment disclosed in these patents allows a user to define programs or routines by block diagrams, or "virtual instruments." As this is done, machine language instructions are automatically constructed which characterize an execution procedure corresponding to the displayed procedure.

Interface cards for communicating the computer with the motor controllers are also available commercially, e.g., from National Instruments Corp.

The receptacle-holding area of the upper support is adapted to removably support a plurality of receptacles for receiving respective reagents from the dispenser array. Along the holding area, means are provided for maintaining each receptacle in a desired location while the support is moved from one place to another. For example, a slightly recessed trough-like region can extend below the uppermost surface of the support, into which the receptacles can be placed. Alternatively, or in addition, mechanical holding means such as clips, brackets, bumpers, framing, VEL-CRO®, or the like, and/or magnetic holding means, such as magnetic strips on the holding-area surface and a magnetically attractable undersurface on the receptacles, or the like, can be employed to maintain the containers in place.

Figure 2:
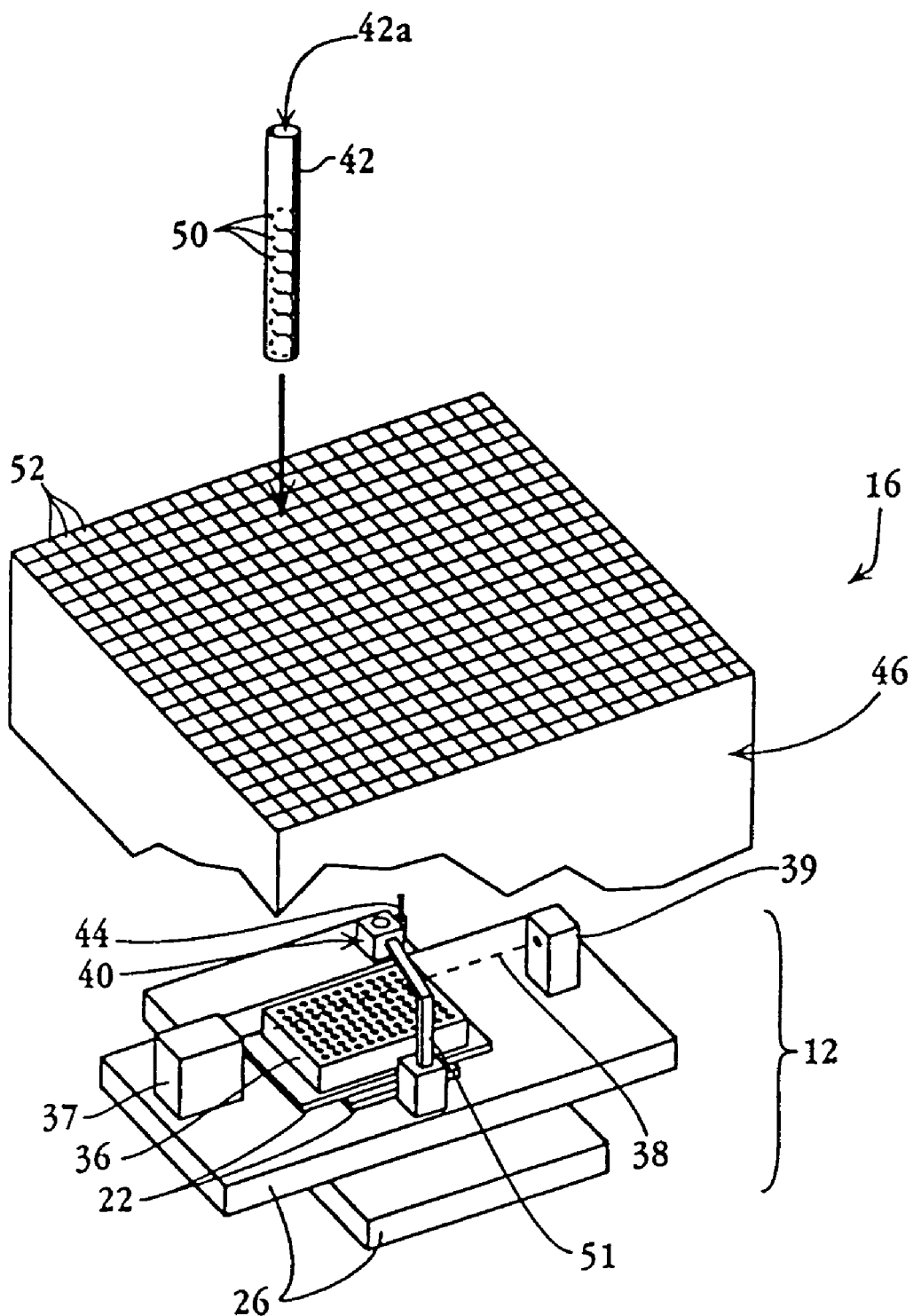
FIG. 2 is a perspective view, with portions broken away, showing additional details of the reagent storage and dispensing system of FIG. 1.
Figure 3:
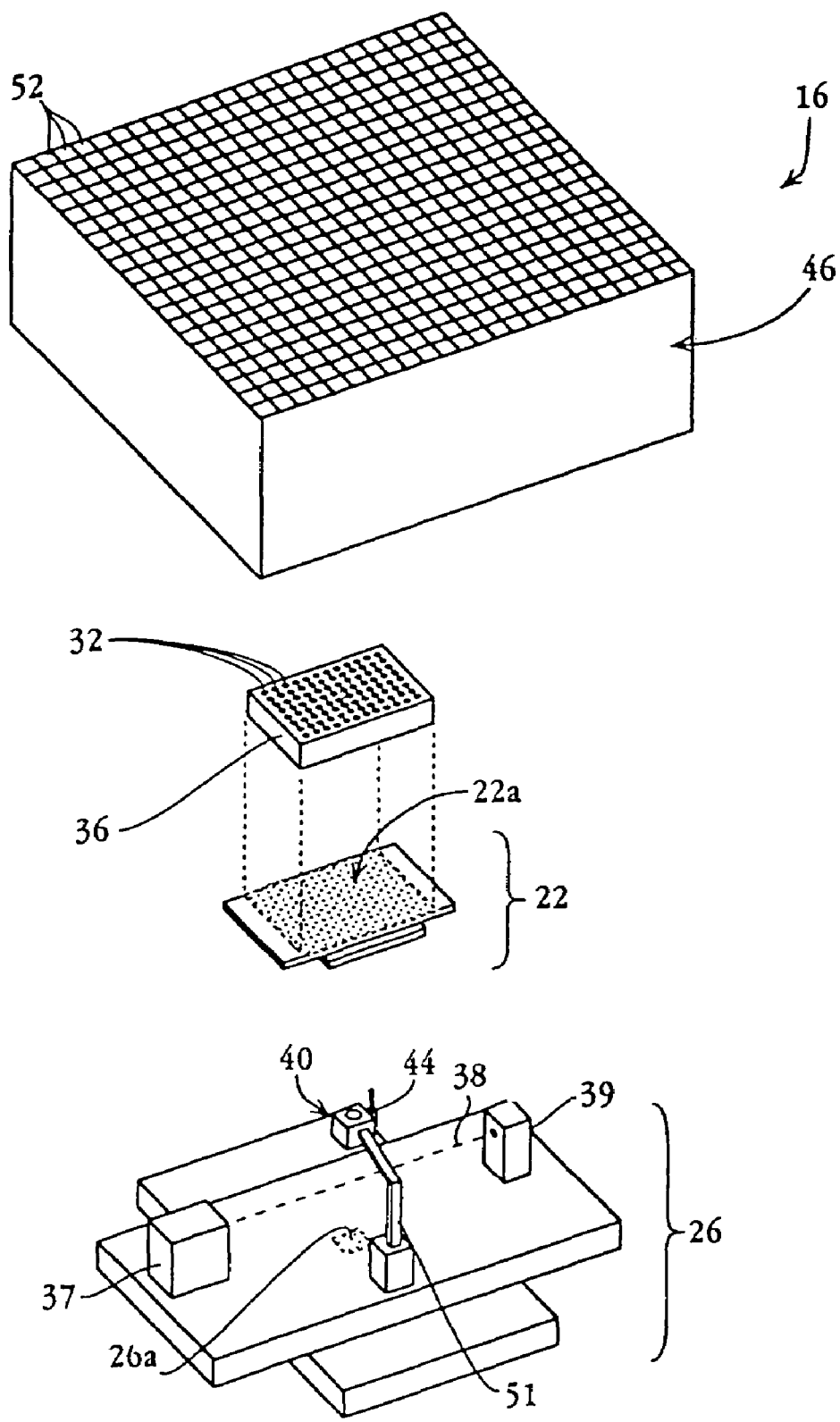
FIG. 3 is an exploded view showing still further details of the reagent storage and dispensing system of FIGS. 1 and 2.

In the embodiment of FIGS. 1-3, the receptacles are provided as an array of spaced-apart receiving wells, such as wells 32, formed in a tray or plate 36. Each of wells 32 has an opening at its upper end, permitting the well to receive and hold a reagent dispensed from above. A spring-loaded plate holder (not shown), attached to the upper surface of support 22 on opposing sides of holding area 22a, prevents plate 36 from sliding across upper support 22 as it is moved.

As previously indicated, lower support 26 is provided with a fixed (constant) reference or target region, such as area 26a visible in FIG. 3. The fixed target region is a specific portion of the lower support (i) that is positionable under any dispenser of the dispenser array, and (ii) over which any selected (variable) site of the receptacle-holding area can be positioned. Typically, placement of the fixed target region will be determined by the presence of one or more elements, discussed below, each having a position and/or operational range of motion that is substantially fixed above a particular area of the lower support's upper surface. For example, the fixed target region can lie under a radiation beam, such as beam 38 in FIGS. 1-3, projectable over the receptacle holding area for detecting the passage of reagent from an overhead dispenser into a receptacle. As another example, the fixed target region can be located below a guide or funnel member, as at 40 in FIGS. 2-3, for channeling reagent dispensed from an overhead dispenser to a selected site on the receptacle holding area. As yet a further example, the fixed target region can be positioned in the vicinity of a release mechanism or actuator, as at 44 in FIGS. 2-3, for causing a selected reagent dispenser to dispense a desired reagent. Where more than one of the above components are employed, they will typically all be located in the general area at or above the fixed target region. Details of such components are discussed more fully below.

Turning now to the reagent dispenser array, each reagent dispenser takes the form of an elongated container, such as cylindrical or tubular container 42 shown poised above array 16 in FIG. 1. The containers can be formed, for example, of plastic, glass, and/or metal, or other material. In one embodiment, each container is a rigid cylinder formed of a metal or metal alloy (e.g., aluminum, an aluminum alloy, or stainless steel), intended for repeated uses. In another embodiment, each container is constructed of a relatively inexpensive material, such as glass or plastic that can be readily disposed of after its contents (reagent) have been exhausted.

By configuring each container with a sufficiently narrow diameter, a high density of such containers can be achieved. For example, various embodiments contemplate from about 2 to 8 containers per $cm^2$, on average, or higher. One preferred embodiment contemplates an average density of between about 3-6 containers per $cm^2$; and most preferably between about 4-5 containers per $cm^2$. In an exemplary arrangement, a plurality of substantially like containers, each having a diameter of less than 1 cm, are disposed with substantially parallel longitudinal axes and at closely spaced positions defining an array. In one particularly preferred embodiment, an array of such containers, each having an outer diameter of about 4 mm, are arranged with a center-to-center spacing between adjacent containers of about 4.50 mm.

Each container is provided with a passageway configured to receive and hold a respective reagent. In the embodiment of FIG. 1, a longitudinally extending lumen, denoted as 42a, holds a plurality of reagent-containing ampules, such as 50. The passageway can be of any horizontal cross-section, such as circular, oval, polygonal, or other cross-section. Optionally, the exposed inner sidewalls of the passageways can be covered with a substantially inert lining material.

A rack or frame, generally denoted as 46, provides a plurality of holding cells, each being configured to support one reagent container therein. In FIG. 1, for example, container 42 can be inserted into one of holding cells 52 of frame 46 by lowering it in the direction of the darkened arrow. The rack can have any number of holding cells. In one embodiment, the number of different reagents held in the rack determines the number of holding cells. That is, there can be a one-to-one correspondence between the number of holding cells and the number of different reagents. For situations requiring a relatively large quantity of a particular reagent, other embodiments provide such reagent in two or more holding cells of the array.

Rack 46 can have tens, hundreds, thousands, tens of thousands, or hundreds of thousands of holding cells. Advantageously, such configurations permit the storage and variable selection of many different reagents. In one particularly preferred embodiment, rack is formed with 10,000 holding cells, each removably supporting a respective reagent container in a substantially upright fashion. In this embodiment, any combination of up to 10,000 different reagents can be dispensed into the wells of a multi-well tray.

It should further be appreciated that a plurality of such racks can be utilized, for example, in an "assembly line" type arrangement. For example, three 10,000 cell racks can be arranged at respective locations along an automated system, each capable of dispensing up to 10,000 different reagents.

The particular form of each reagent stored and dispensed in accordance with the teachings of the invention is not critical, provided only that it is compatible with the storage and dispensing means. The reagent, which can be a single substance or a grouping of different substances, can be provided, for example, as a solid, liquid, powder, emulsion, suspension or substantially any combination thereof. In one embodiment, a coating material is applied to a reagent core to form particulates, pills, beads or tablets. The coating can be dissolvable or swellable to permit access to the reagent under controllable conditions (e.g., upon exposure to a particular solvent).

Guidance for preparing coated micro-particles (beads) is provided, for example, in: [1] R. Pommersheim, H. Lowe, V. Hessel, W. Ehrfeld (1998), "Immobilation of living cells and enzymes by encapsulation," Institut für Mikrotechnik Mainz GmbH, IBC Global Conferences Limited; [2] F. Lim A. Sun (1980), *Science* 210, 908; [3] R. Pommersheim, J Schrezenmeir, W. Vogt (1994), "Immobilization of enzymes and living cells by multilayer microcapsules" *Macromol Chem. Phys* 195, 1557-1567; and [4] W. Ehrfeld, V. Hessel, H. Lehr, "Microreactors for Chemical Synthesis and Biotechtechnology—Current Developments and Future Applications" in: *Topics in Current Chemistry* 194, A. Manz, H.

Becker, Microsystem Technology in Chemistry and Life Science, Springer Verlag, Berlin Heidelberg (1998), 233-252; each expressly incorporated herein by reference.

In another embodiment, a plurality of bead-like particles act as solid supports for the reagents. For example, reagents can be synthesized on the beads, or absorbed thereto. In still a further embodiment, a slurry or dispersion comprised of a reagent and binding material is used to form a plurality of bead-like particles, with each individual bead having a substantially homogenous consistency.

A plurality of different reagents can be formed into respective collections or groups of reagent beads, or "lots." For example, 10,000 different reagents can be formed into 10,000 different bead lots, with each lot comprised of a plurality of substantially like beads carrying a respective reagent. Beads from each lot can then be loaded into respective dispensers of the dispenser array.

In one embodiment, a plurality of bead lots are formed, wherein each bead includes a reagent core covered with a coating material, such as a gelatin, having well-defined physical and chemical properties. Preferably, in this embodiment, all beads in all lots bear substantially the same outer coating (i.e., a "generic" coating). It should be appreciated that this arrangement reduces the risk of equipment contamination due to contact with the reagents. If any residues are left behind as the reagents move through the system, such residues will all be of the same coating material. Preferably, the coating material is chosen so that any residues are innocuous to the system.

Further regarding reagent-carrying beads, the beads can be formed with a diameter slightly less than that of one of the passageways of the dispenser array, so that the beads can be stacked in each container, one on top of the other, for gravity-fed dispensing. For example, beads having a diameter of between about 3.50-3.90 mm, and preferably about 3.70 mm, can be stacked in a container having a passageway with a diameter of about 4 mm.

Figure 4:
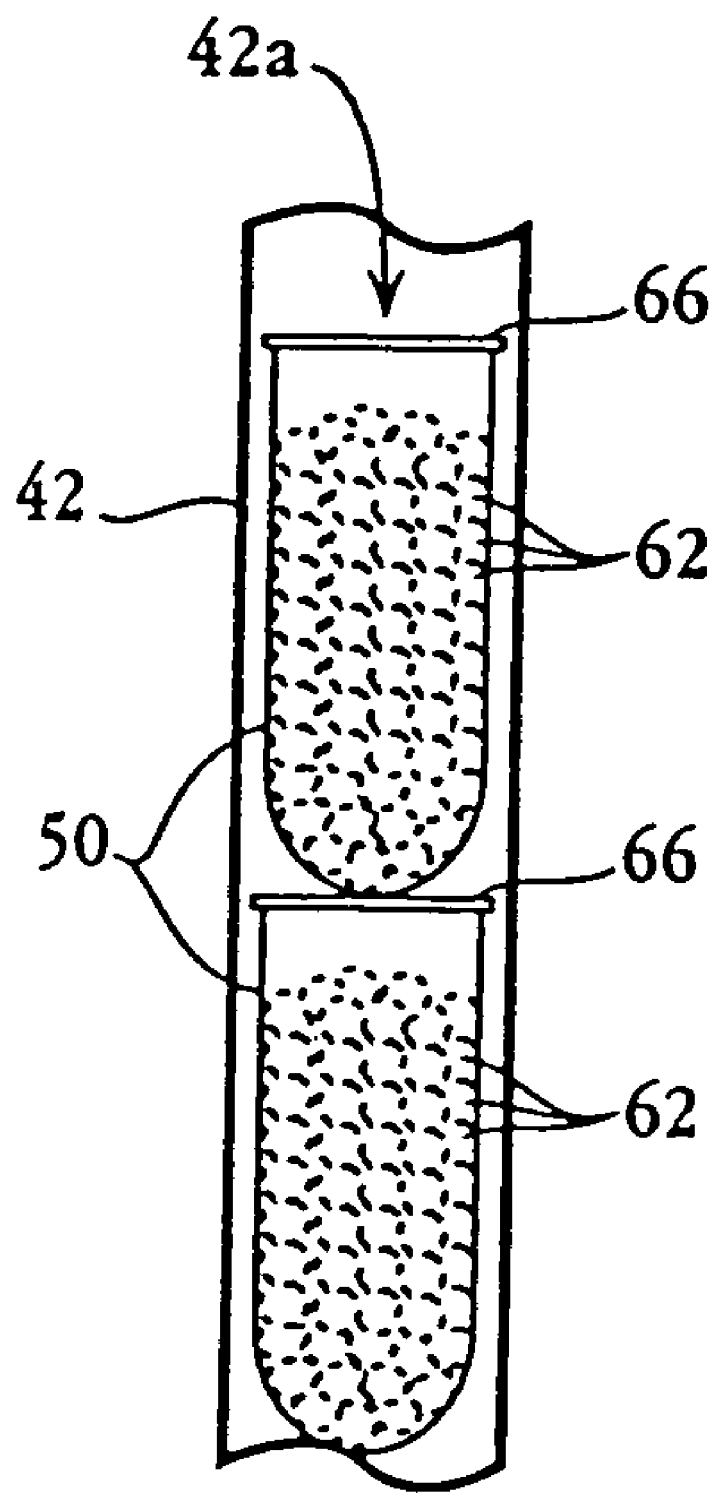
FIG. 4 is a partial side-sectional view of a dispenser of the invention holding a plurality of reagent-containing ampules.

Alternatively, the beads can be relatively small, e.g., each having a diameter of less than about 1 mm. In one preferred embodiment, each bead has a diameter of between about 275-325 μm, and preferably about 300 μm. A plurality of such beads can be placed in a capsule or ampule to be dispensed as a unit. For example, hundreds or thousands of beads from the same or substantially identical lots can be packed into plastic ampules. The exemplary arrangement of FIG. 4 shows reagent-carrying beads 62 disposed in bullet-shaped ampules 50. The various passageways in the dispenser array can be loaded with a plurality of such ampules, each containing beads from respective lots. As best seen in FIG. 4, the ampules can be dimensioned to move downward through the passageways under the force of gravity in a substantially single-file fashion.

The ampules can be provided with a cover member over an upper opening thereof. The cover member can be, for example, a removable cap or dome having an open end configured to fit snugly about the upper region of an ampule. Or, a frangible sheet-like film or membrane, such as membranes 66 in FIG. 4, can be applied to an upper rim or lip surrounding the upper opening of each ampule. Access to the beads can be gained, for example, by removing or rupturing the membrane cover.

In one embodiment, the cover over each ampule forms a substantially airtight seal, protecting the reagent contents of the ampule from the ambient atmosphere. The seal can be effected, for example, using conventional adhesives or by heating-sealing techniques. The sealed ampules can further contain an inert gas, such as nitrogen or the like.

Substantially any reagent can be stored and dispensed using the system of the present invention. According to one preferred embodiment, the reagent in each dispenser includes components useful for real time fluorescence-based measurements of nucleic acid amplification products (such as PCR) as described, for example, in PCT Publication WO 95/30139 and U.S. patent application Ser. No. 08/235,411, each of which is expressly incorporated herein by reference.

In one embodiment, each container holds an analyte-specific reagent effective to react with a selected analyte that may be present in a sample. For example, for polynucleotide analytes, the analyte-specific reagent can include first and second oligonucleotide primers having sequences effective to hybridize to opposite end regions of complementary strands of a selected polynucleotide analyte segment, for amplifying the segment by primer-initiated polymerase chain reaction. The analyte-specific detection reagent can further include a fluorescer-quencher oligonucleotide capable of hybridizing to the analyte segment in a region downstream of one of the primers, for producing a detectable fluorescent signal when the analyte is present in the sample.

An accession or tracking number can be printed on each container, identifying the reagent contained therein. For those embodiments employing ampules to hold the reagents, each ampule can bear such a tracking number. With regard to the latter, the containers can be formed with window regions through which the tracking numbers on the ampules can be observed. The window regions can be of a transparent material, such as glass or plastic, or they can be openings or notches formed in the sidewalls of the containers.

Preferably, each tracking number is provided in a machine-readable format, such as a bar code. An operator can manually scan the bar codes, or they can be scanned in an automated fashion using robots. In one embodiment, a robot picks up a container from a tray of reagent tubes and wands a bar code to learn and/or confirm the identity of the reagent held therein. Using the scanned information, a control computer instructs the robot to place the tube in a designated holding cell of a rack.

Controllable dispensing of each reagent is provided by a gate mechanism located at a lower outlet region of each dispenser. Each gate mechanism is independently operable between (i) an opened condition permitting passage of a respective reagent through the outlet region, and (ii) a closed condition whereat such passage is blocked. The particular construction of the gate mechanism is not critical, provided only that it is capable of retaining the reagent held in the respective container until such time that it is desired to dispense the reagent. Additionally, each gate mechanism is preferably operable on an individual basis, so that the various reagents can be dispensed one at a time.

Several exemplary gate mechanisms for use in connection with various types of reagents will now be described.

According to one embodiment, each gate mechanism includes a magnetic pinch valve having first and second magnets that are pivotally mounted in facing relation at a respective container outlet region. Generally, the pinch valve magnets have lower, confronting north and south pole regions that are urged toward one another by magnetic forces, thereby normally disposing the gate mechanism in a "closed" condition. Additional structure may be included to supplement or enhance such normal positioning of the pivotal magnets.

Figure 5A:
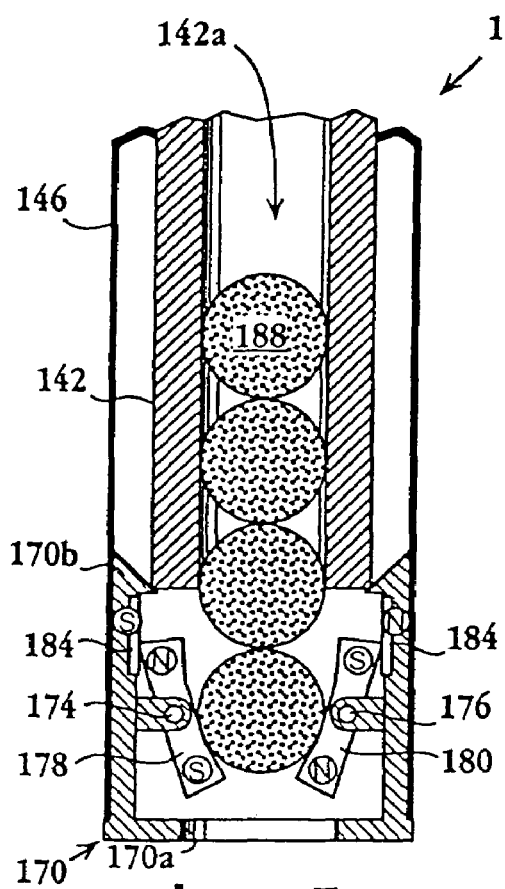
FIGS. 5(A) and 5(B) are vertical and horizontal cross-sectional views, respectively, showing a magnetic pinch valve blocking the passage of reagent beads from a dispenser, in accordance with one embodiment of the present invention.
Figure 6A:
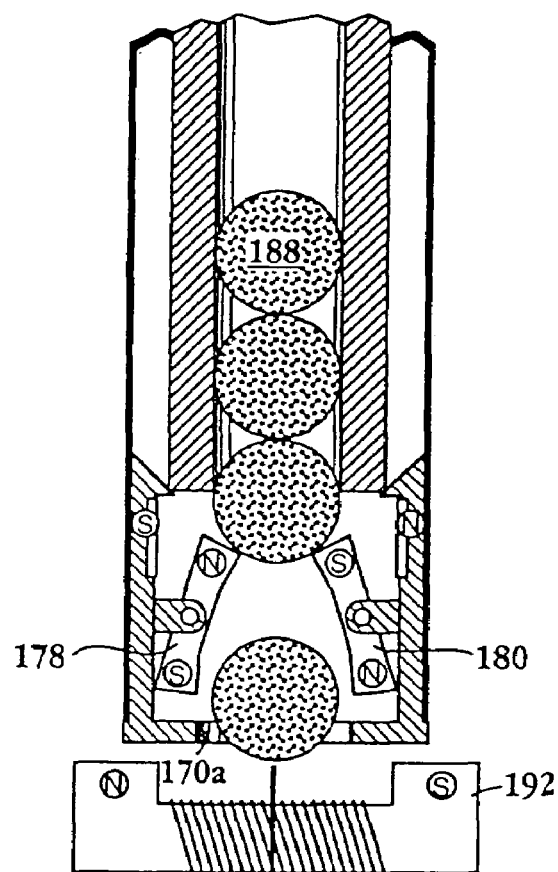
FIGS. 6(A) and 6(B) are vertical and horizontal cross-sectional views, respectively, showing an electromagnet inducing the magnetic pinch valve of FIGS. 5(A) and 5(B) to permit the passage of reagent beads.
Figure 5B:
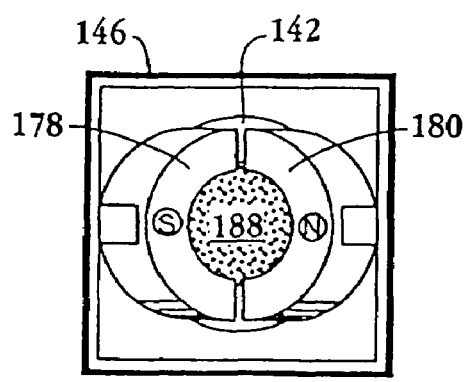
Figure 6B:
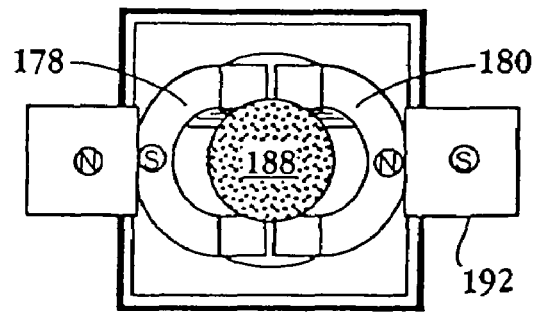

FIGS. 5 and 6 show one particular embodiment of a magnetic pinch valve that is especially useful for dispensing reagent-carrying beads. Here, a supportive insert or plug, such as 170, is disposed in a lower region of each holding cell 152 of rack 146. Frictional engagement of the insert's outer sidewall with the inner sidewall of a respective holding cell can hold the insert in place. Adhesives or other retaining means may be employed to ensure the long-term placement of each insert. The lower end of an elongated container 142, containing reagent beads 188, rests on an upper, inwardly flanged portion of insert 170b. Insert 170 provides pivot points, denoted as 174 and 176, on opposing inner sidewall portions to which respective permanent magnets 178, 180 pivotally attach at their midregions, e.g., by way of pivot pins. As best seen in FIGS. 5(B) and 6(B), each pivotal magnet 178, 180 is substantially C-shaped in horizontal cross-section. Pivotal magnets 178, 180 are oriented such that their upper and lower end regions are of opposite polarity. A third permanent magnet, denoted as 184, is fixedly positioned along a sidewall portion of insert 170, above pivot points 174, 176. One end of this stationary magnet 184 is disposed adjacent an upper region of one of the pivotal magnets, 178 or 180; and the other end of magnet 184 is disposed adjacent an upper region of the other pivotal magnet. Stationary magnet 184 is oriented such that the polarity of each such end is opposite that of the upper region of the pivotal magnet adjacent thereto. Accordingly, in the normal state, the upper region of each pivotal magnet 178, 180 is attracted to an adjacent portion of the sidewall-mounted magnet 184 and, at the same time, the confronting north and south pole regions of the pivotal magnets are attracted toward one another. In response, magnets 178,180 pivot about their respective pivot points 174, 176 so that their lower north and south pole regions swing toward one another; thereby assuming the closed condition, as shown in FIGS. 5(A) and 5(B). In the closed condition, the outlet region is constricted such that the reagent beads 188 are not able to fall out.

To release a reagent bead, a release mechanism is moved to a position under the outlet region of a selected container. The release mechanism is operable to overcome the closing force that normally prevents the egression of reagent beads. In the embodiment of FIGS. 5-6, an electromagnet 192 is used as the release mechanism. Electromagnet 192 has spaced-apart south and north pole portions disposed to attract the opposing north and south pole lower regions of pivotal magnets 178, 180, respectively, in a direction away from one another. The magnetic force generated upon activating electromagnet 192 is sufficient to overcome the previously-described normal closing force, thereby swinging the lower regions of pivotal magnets 178, 180 apart so that one of the beads 188 can fall through a central opening 170a at the bottom of insert 170. As best seen in FIG. 6(A), upon swinging the lower regions of pivotal magnets 178, 180 apart, the upper regions swing toward one another, thereby blocking the passage of any additional beads 188. Once a bead has been dispensed, electromagnet 192 can be deactivated, permitting the gate mechanism to return to the closed position, as shown in FIGS. 5(A)-5(B). Electromagnet 192 can then be moved to another container for dispensing another reagent. It should be appreciated that this arrangement allows for the realization of controllable, single-bead dispensing.

Figure 7A:
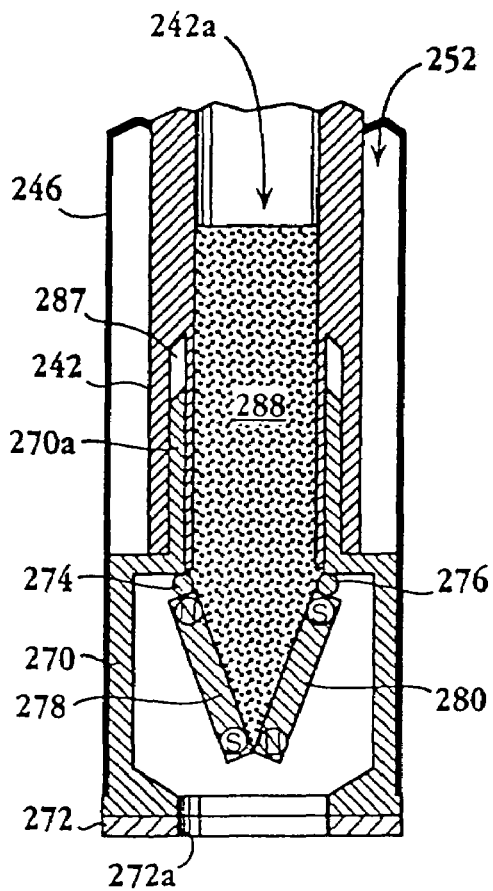
FIGS. 7(A) and 7(B) are vertical and horizontal cross-sectional views, respectively, showing a magnetic pinch valve blocking the passage of a fluidic reagent from a dispenser, in accordance with a further embodiment of the present invention.
Figure 8A:
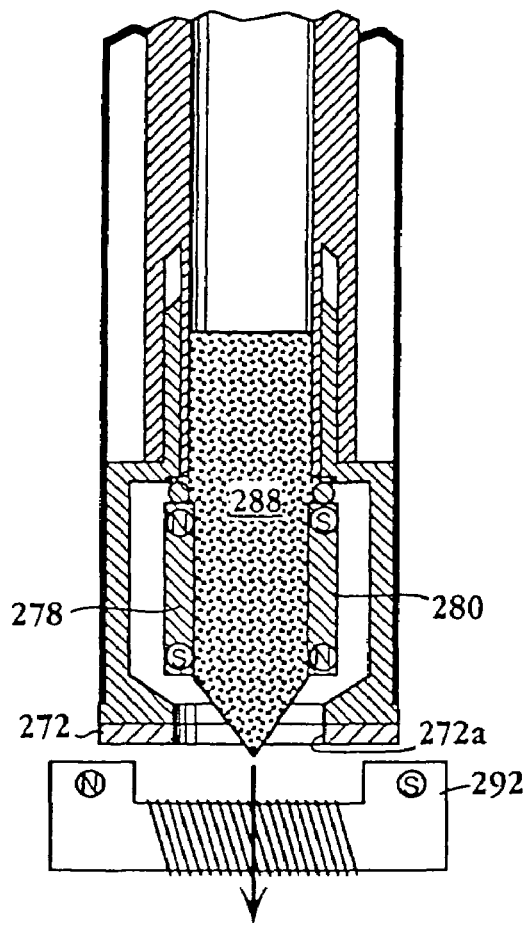
FIGS. 8(A) and 8(B) are vertical and horizontal cross-sectional views, respectively, showing an electromagnet inducing the magnetic pinch valve of FIGS. 7(A) and 7(B) to permit the passage of an aliquot of fluidic reagent.

FIGS. 7 and 8 show an embodiment of a pinch valve especially useful for dispensing a fluidic reagent. In this embodiment, two substantially planar, permanent magnets 278, 280 attach at their uppermost ends to a support member 270, for swinging motion about respective pivotal connections 274, 276. As best seen in FIGS. 7(A) and 8(A), the pivotal connections 274, 276 are disposed on opposing sides of a lowermost opening of elongated container 242. Support member 270, in turn, is fixed to a lower end region of container 242. In this regard, an annular cavity 287 extends upwardly from a lowermost rim or lip of container 242, circumscribing longitudinal passageway 242a. An upstanding cylindrical collar 270a, formed at the top of support member 270, is configured to fit snugly into cavity 287. Collar 270a can be maintained in cavity 287 by frictional forces and/or adhesive agents. A plate 272 is secured against a lowermost end of holding cell 252 to provide a lower foundation for supporting the container and gate assembly therein.

Figure 7B:
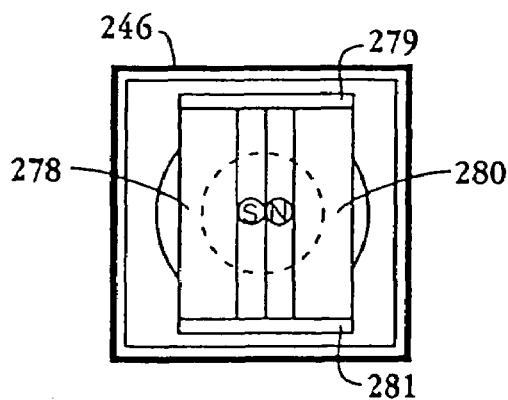
Figure 8B:
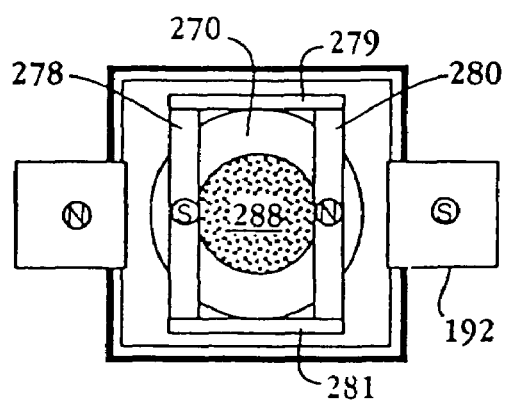

Gasket members 279, 281 (FIGS. 7(B) and 8(B)) are affixed to opposite inner sidewall portions of support member 270. Gasket members 279, 281 provide opposing planar surfaces positioned for sliding, substantially fluid tight, contact with the lateral side-edges of pivotal magnets 278, 280. The opposing planar surfaces of gasket members 279, 281 can be formed of a hydrophobic material, and/or treated to exhibit hydrophobic characteristics, to discourage undesired leakage of the liquid reagent 288.

Similar to the previous embodiment, pivotal magnets 278, 280 are oriented such that they having lower end regions of opposite polarity. So arranged, the lower ends of pivotal magnets 278, 280 are normally attracted such that they swing toward one another and make contact, establishing a substantially fluid-tight seal (i.e., a "closed" position). In this regard, one or both magnets 278, 280 can bear a polymeric coating (not shown) along the region of contact to assist in the formation of the fluid-tight seal.

To release the liquid reagent, a release mechanism is moved to a position under the outlet region of a selected container. With reference now to FIGS. 8(A)-8(B), an electromagnet 292 is employed as the release mechanism. Electromagnet 292 has spaced-apart south and north pole portions disposed to attract the opposing north and south pole lower regions of pivotal magnets 278, 280, respectively, in a direction away from one another. The magnetic force generated upon activating electromagnet 292 is sufficient to overcome the previously-described normal closing force, thereby swinging the lower regions of pivotal magnets 278, 280 apart so that an aliquot of fluidic reagent 288 can fall through a central opening 272a in plate 272. The duration of activation of electromagnet 292 can be used to gauge the amount of liquid reagent dispensed. When electromagnet 292 is turned off, the normal attraction between the opposing lower end regions of magnets 278, 280 returns the valve to a closed position.

Figures 9A, 9B:
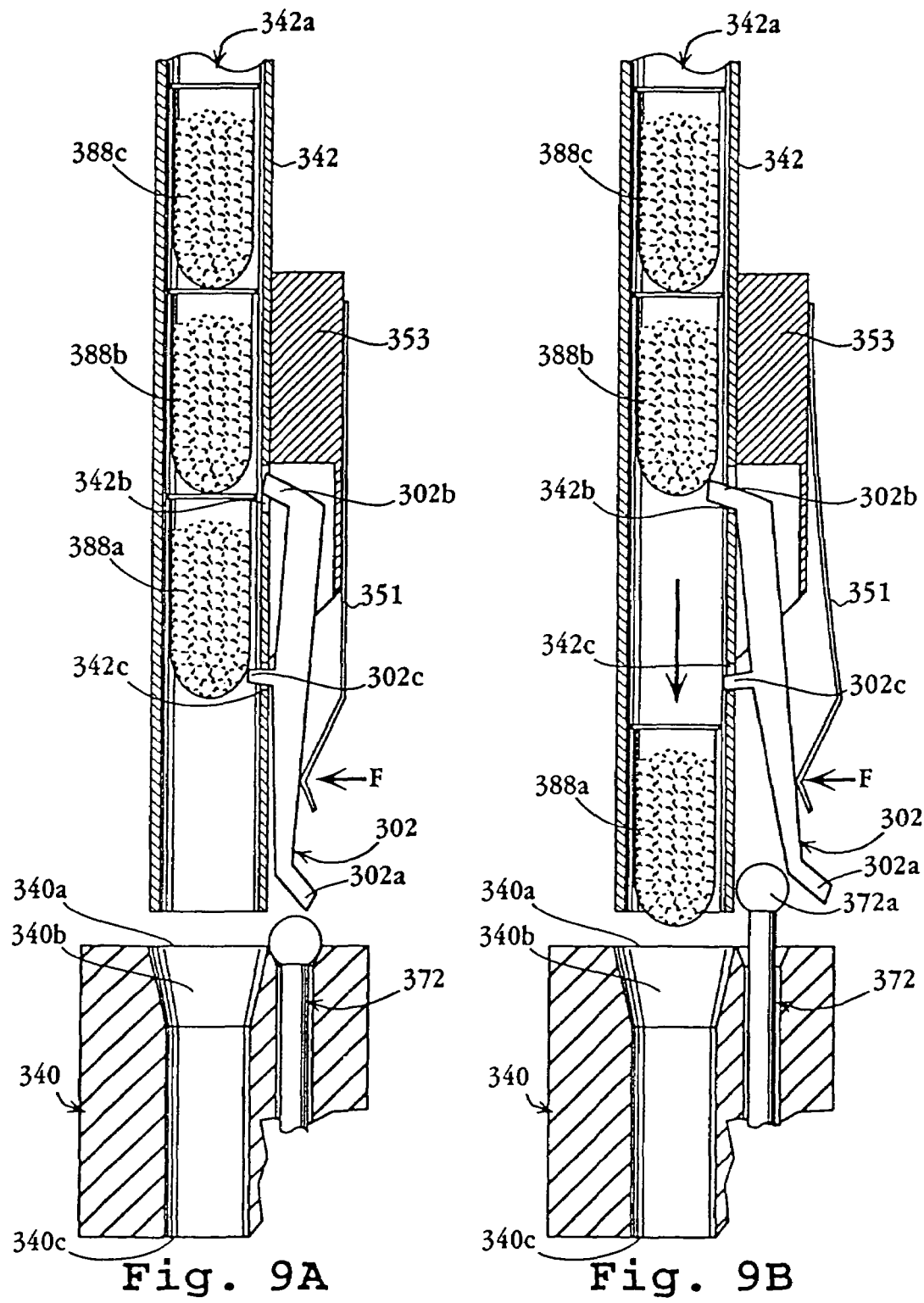
FIG. 9(A) is a side cross-sectional view showing a spring-biased lever blocking the passage of reagent-carrying ampules from a dispenser, in accordance with one embodiment of the present invention.
FIG. 9(B) is a side cross-sectional view showing a rod-like actuator deflecting the spring-biased lever of FIG. 9(A), so that a single reagent-carrying ampule can fall from the dispenser into an underlying guide or funnel member.

In another embodiment, each gate mechanism is a resiliently deflectable lever having a protrusion that normally extends into a respective outlet region. In an exemplary arrangement, as illustrated in FIGS. 9(A)-9(B), an elongated lever, indicated generally by the reference numeral 302, extends longitudinally along the outer sidewall of container 342, proximate the container's lower outlet region. Upper and lower nubs or protrusions, denoted respectively as 302b and 302c, project outwardly from one side of lever 302, towards container 342. Container 342, in turn, is provided with upper and lower bores, indicated respectively as 342b and 342c, that extend fully through its sidewall at locations adjacent to lever 302. More particularly, each of bores 342b, 342c is positioned in alignment with a respective one of protrusions 302b, 302c, and is configured to removably receive such protrusion therein.

A resilient spring member, such as leaf spring 351, is secured at one of its ends to a support structure 353 that is fixedly positioned near the lower outlet region of container 342. The other end of leaf spring 351 is disposed to act against a side of lever 302, opposite container 342. Leaf spring 351 provides a normal biasing force, along the direction "F," that presses the lower end region of lever 302 against container 342. Under these circumstances, lower protrusion 302c extends through lower bore 342c and into passageway 342a at the container's lower outlet region, as shown in FIG. 9(A). In this "closed" position, lower protrusion 302c blocks the egression of any reagent-carrying ampules 388a-388c. Upper protrusion 302b, on the other hand, is positioned outside of passageway 342a in the normal, closed position.

To release an ampule, a release mechanism is moved to a position under the outlet region of a selected container. The release mechanism is operable to overcome the closing force that normally prevents the egression of ampules. With reference to FIGS. 9(A) and 9(B), an elongated rod 372 can be employed as the release mechanism. Rod 372 is adapted for reciprocal linear motion between (i) a retracted position, whereat rod 372 is positionable below a selected lever, such as lever 302 in FIG. 9(A), to (ii) an extended position, whereat a rounded-head portion of rod, denoted at 372a, can abut and press against a lower, outwardly-angled cam surface of lever, as at 302a in FIG. 9(B), thereby deflecting lever 302 away from container 342. Such motion of rod 372 can be effected, for example, by providing rod at the end region of a movable plunger extending from a conventional solenoid assembly.

Notably, when lever 302 is deflected in the manner just described, lower protrusion 302c is withdrawn from passageway 342a, permitting the bottommost reagent-carrying ampule 388a to fall from the container's lower outlet region. Also during such deflection, upper protrusion 302b is received within upper bore 342b such that it extends into passageway 342a, preventing the egression of any remaining ampules 388b-388c. Upon returning rod 372 to its retracted position, lever 302 reassumes its normally closed position, as in FIG. 9(A), preventing the passage of any ampules. It should be appreciated that this arrangement permits controllable, single-ampule dispensing.

In an alternative embodiment, similar to the embodiment just described, the release mechanism operates according to magnetic principles. In an exemplary arrangement (not shown), the lower end of the resiliently deflectable lever and the upper head portion of reciprocally movable rod are magnetically polarized, or polarizable, to exhibit the same polarity (e.g., both being "N"). The lever can be deflected by moving the rod into proximity with the lever's lower end, so that the like magnetic pole portions repel one another. Notably, contact between the rod and the lever is not required in this embodiment. The magnetic repulsion is sufficient to deflect the lever away from the container, thereby permitting a reagent-carrying ampule to fall from the container's lower outlet region.

Any of the above-described release mechanisms can be adapted for variable positioning along a generally horizontal plane under the dispenser array by mounting it to the upper surface of the lower xy stage. In this regard, a mounting assembly, such as bracket 51 of FIGS. 1-3, can be used to hold the release mechanism. In this embodiment, one end of bracket 51 is affixed to the upper surface of lower xy stage 26. The other (free) end of bracket 51 extends into the region between the platform assembly 12 and the dispenser array 16, whereat the release mechanism is supported, as schematically indicated at 44.

A detection assembly can be provided for detecting the passage of reagent into a receptacle from a selected overhead dispenser. In the exemplary arrangement of FIGS. 1-3, the region between a radiation source or emitter, such as laser 37, and a radiation sensor, as at 39, defines a detection zone. In this embodiment, both laser 37 and sensor 39 are fixedly positioned at respective locations on the upper surface of the lower xy stage 26, on opposing sides of upper xy stage 22. This construction permits movement of the detection zone along a generally horizontal plane under dispenser array 16 with movement of the lower xy stage 26. Thus, by moving xy stage 26 in an appropriate manner, the detection zone can be placed under any selected dispenser of array 16. A narrow-width beam, indicated at 38, can be directed from laser 37 along the detection zone and detected by sensor 39. An interruption in the beam 38 indicates the passage of a reagent from a dispenser above the detection zone.

Lasers and sensors, suitable for use in practicing the invention, are available commercially, for example, from Edmund Scientific (Barrington, N.J.). A particularly preferred diode laser, for use as a radiation emitter, is made by Coherent, Inc. (Auburn, Calif.).

In addition to detecting the passage of reagent, beam 38 can also be employed to confirm the identity of a dispensed reagent. For example, beam 38 can "double" as a bar-code scanner. In one embodiment, each reagent-carrying ampule bears a bar code that is unique to the particular type of reagent held therein. As a dispensed ampule passes through the beam, the bar code is read and the information is passed on to the control computer. The computer can then positively identify the dispensed reagent, and take appropriate corrective measures in the event of a dispensing error.

A guide or funnel member can be provided in the region between the dispenser array and the platform assembly for channeling reagent dispensed from an overhead dispenser to a selected site on the receptacle-holding area of the upper xy stage. In the exemplary arrangement of FIGS. 1-3, such a guide member, indicated schematically at 40, is fixedly positioned relative to the upper surface of lower support by way of mounting bracket 51. This construction permits movement of the guide member 40 along a generally horizontal plane under the dispenser array 16 with movement of the lower xy stage 26.

Typically, in operation, guide member 40 will be positioned under a selected dispenser of array 16. A selected receptacle, such as a particular well of multi-well plate 36, will be positioned under the guide member by appropriately moving the upper xy stage 22. Such positioning of the guide member and the receptacle will preferably occur simultaneously. A dispensed reagent, then, will fall through a central, vertically extending channel of guide member 40 on its way from the selected dispenser to the selected receptacle.

In one particular embodiment, shown in FIGS. 9(A) and 9(B), a guide member, denoted as 340, includes (i) an upper opening 340a, (ii) a lower opening 340c, smaller than the upper opening 340a, and (iii) a conical or funnel-shaped portion 340b, between the upper and lower openings. Also in this embodiment, it should be noted that the guide member 340 and reciprocally-movable rod 372 are conveniently provided together in a common housing.

At this point, the significance of the fixed target region of the lower support can be well appreciated. The fixed target region is primarily a reference point that, when positioned under a selected dispenser, facilitates the proper and simultaneous positioning of one or more additional components thereunder. For example, with reference to the embodiment of FIGS. 1-3, each of the following elements is positioned at an appropriate location with respect to a selected container, as described, upon moving the fixed target region 26a to a location under such container:

(i) radiation beam 38 is located under the selected container so that any reagent dispensed from the container will break the beam;

(ii) guide or funnel member 40 is disposed with its upper, large opening axially aligned with the lower outlet region of the selected container so that dispensed reagent will fall therein; and (iii) release mechanism 44 is positioned proximate a normally closed gate mechanism at the lower outlet region of the selected container.

Moreover, a selected well of multi-well plate 36, supported at the receptacle-holding area of the upper xy stage 22, can be moved to a position over the fixed target region while the fixed target region is being moved under the selected receptacle as just described. In this way, the receptacle, too, can be quickly and accurately positioned to receive a dispensed reagent.

As with the xy stages 22, 26, operation of the various components and sub-assemblies described above can be controlled and orchestrated using the LABVIEW® or LAB-WINDOWS® software from National Instruments (Austin, Tex.) by techniques known in the art.

In a typical use, an array of holding cells 52 in rack 46 are loaded with respective containers 42, each holding a particular reagent. A data set or table is created comprised of values identifying each location or address of the holding-cell matrix with its particular resident reagent. The data set is stored electronically on a drive unit accessible to a control computer. The reagents are maintained in rack 46 until dispensed, e.g., as follows.

Multi-well plate 36 is placed on receptacle-holding area 22a of upper xy stage 22. A plurality of reagents, stored in rack 46, are selected for dispensing into chosen wells 32 of plate 36, and this information is fed to the control computer. The computer accesses the data set of location information to determine which containers hold the selected reagents, and a loading sequence is constructed and held in memory. The computer signals the motor controller to move lower xy stage 26 to a location whereat its fixed target region 26a is disposed under the first container of the loading sequence. At the same time, upper xy stage 22 positions a selected target region of the receptacle-holding area 22a, underlying a chosen well of multi-plate 36, over the fixed target region 26a. Together, these steps serve to position radiation beam 38, guide member 40, and release mechanism 44 at appropriate respective locations proximate a lower outlet region of the container, as well as to position the chosen well of plate 36 under the container. The computer then signals activation of release mechanism 44, causing the gate mechanism at the lower outlet region of the container to open and dispense an aliquot of its respective reagent into the chosen well of plate 36. A correctly dispensed substance will briefly prevent radiation beam 38 from reaching sensor 39, indicating successful dispensing. If radiation beam 38 is not interrupted, as expected, an error in dispensing is recorded and a further attempt at dispensing the reagent can then be made, as desired. After the first reagent has been dispensed, the next reagent of the loading sequence can be dispensed in a like manner.

Figure 10:
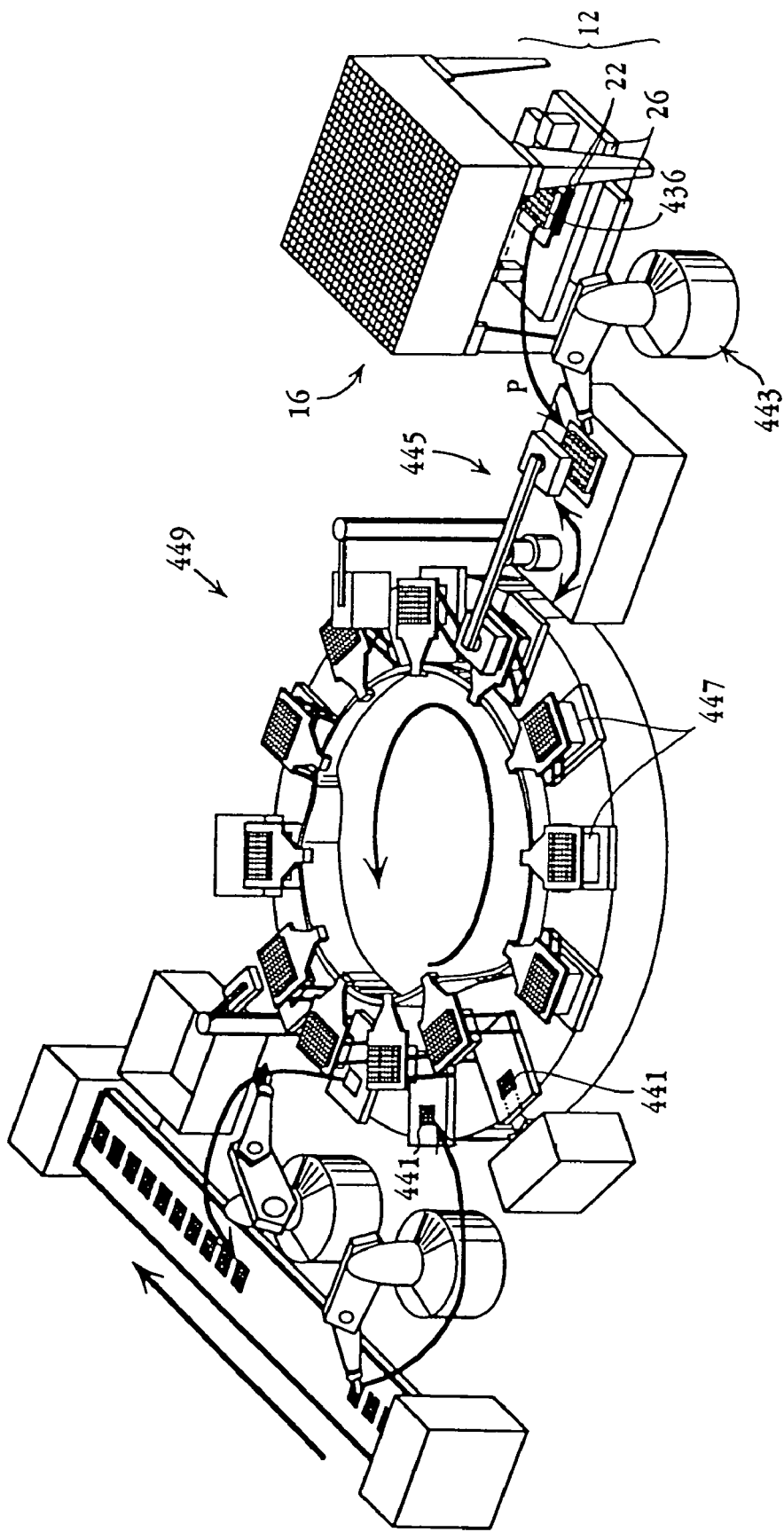
FIG. 10 is a perspective view of the reagent storage and dispensing system of the present invention in the context of a larger system for loading microcard wells with reagent-carrying beads.

In one preferred embodiment, the dispensing system of the present invention is utilized as a sub-assembly in a larger system for loading an array of very small wells in a microcard with respective reagents. In the exemplary arrangement of FIG. 10, a 384-well plate, denoted as 436, serves as a source of reagent for serially loading target 384-well microcards, such as 441, supported for movement on a carousel assembly 449. The wells of both the plate and the microcards are disposed in 16×24 arrays, spaced about 4.5 mm center-to-center. The wells of the plate, however, have a greater diameter than the wells of the microcards. For example, each well of the plate can be configured with a diameter of about 3 mm, while each well of the microcards can be formed with a diameter of about 1 mm.

Generally, each well of the multi-well plate 436 is loaded with a respective reagent-carrying ampule, in accordance with the foregoing detailed description. A robot, such as 443, then moves the ampule-loaded plate, in the direction of darkened arrow "P," to a pick-and-place unit 445. Pick-and-place unit 445 simultaneously retrieves a reagent bead from each ampule in the plate, and retains the beads at spaced-apart locations defining an array corresponding to the plate and microcard arrays. Pick-and-place unit 445 then rotates about its central axis to position the retained beads over the wells of a microcard supported on the carousel at a location directly adjacent thereto, at which point it releases the beads. A bead distributor, such as 447, interposed between pick-and-place unit 445 and the target microcard, separately channels each released bead into its designated well. The loaded microcard wells can then be used to carry out a desired assay or reaction, such as real-time PCR.

Additional details of the micro-card loading system are provided in co pending application Atty. Docket No. 0550-0076/4424, filed concurrently herewith and expressly incorporated herein by reference.

The many benefits offered by the storage and dispensing system of the present invention can now be appreciated. For example, simultaneous movement of the upper and lower supports (e.g., xy stages) allows quick and accurate positioning of the various system components. Moreover, once a desired receiving receptacle is positioned under a selected dispenser, the release mechanism and detection beam can operate immediately to dispense the substance. Consequently, serial dispensing of a plurality of substances can be accomplished in a very rapid manner.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

What is claimed:

1. A system for storing and dispensing a plurality of solid reagents, comprising:

an addressable array of solid reagent dispensers;

a gate mechanism at a lower outlet region of each dispenser, each gate mechanism being independently operable between (i) an open condition permitting passage of a respective solid reagent through said outlet region, and (ii) a closed condition whereas such passage is blocked;

a first support disposed below said array; and a second support mounted on said first support, said second support having a holding area for receiving a plurality of receptacles;

wherein (i) said first support is variably positionable, permitting placement of a fixed target region thereof directly under any selected one of said dispensers in said array, and (ii) said second support is variably positionable, permitting placement of any selected target site of said holding area directly over said fixed target region.

2. The system of claim 1, wherein said first and second supports are independently operable xy stages.

3. A system for storing and dispensing a plurality of solid reagents, comprising:
an addressable array of solid reagent dispensers;
a gate mechanism at an outlet region of each dispenser, each gate mechanism being independently operable between (i) an opened condition permitting passage of a respective solid reagent through said outlet region and (ii) a closed condition wherein said passage is blocked;
a first support disposed adjacent said array; and
a second support mounted on said first support, said second support having a holding area for receiving a plurality of receptacles, wherein (i) said first support is variably positionable to permit placement of a fixed target region thereof in alignment with any selected one of said dispensers in said array, and (ii) said second support is variably positionable to permit placement of any selected target site of said holding area in alignment with said fixed target region.

4. The system of claim 3, wherein said dispensers are elongated containers, each having a longitudinally extending passageway configured to receive and hold a respective solid reagent when said gate mechanism is in the closed condition.

5. The system of claim 4, further comprising a rack having an array of at least about 100 holding cells, each holding cell being configured to removably support one of said containers in a substantially upright fashion.

6. The system of claim 5, wherein said holding cells are disposed at an average density of at least about 3 holding cells per cm$^2$.

7. The system of claim 6, wherein said array includes at least about 500 holding cells; and wherein said holding cells are disposed at an average density of at least about 4 holding cells per cm$^2$.

8. The system of claim 7, wherein said array includes at least about 1,000 holding cells.

9. The system of claim 8, wherein said array includes at least about 10,000 holding cells.

10. The system of claim 9, wherein said array includes at least about 100,000 holding cells.

11. The system of claim 4, further comprising a plurality of different solid reagents disposed in said dispenser passageways.

12. The system of claim 11, wherein each of said passageways contains a solid reagent that is unique to said array.

13. The system of claim 11, further comprising a plurality of solid reagent bead lots, each lot comprised of a plurality of substantially similar reagent beads and moveable through said outlet region.

14. The system of claim 13, wherein each reagent bead has a diameter of less than about a millimeter.

15. The system of claim 11, wherein the plurality of different solid reagents comprises particulate reagents.

16. The system of claim 11, wherein the plurality of different solid reagents comprises powder reagents.

17. The system of claim 11, wherein the plurality of different solid reagents comprises beads.

18. The system of claim 3, wherein said first and second supports are independently operable xy stages.

19. The system of claim 3, wherein each gate mechanism is subject to a normal biasing force that urges it to the closed position, thereby preventing the passage of a solid reagent through a respective outlet region.

20. The system of claim 19, further comprising a release mechanism positionable near any one of said gate mechanisms and operable to apply a secondary force of a magnitude and direction effective to override the normal biasing force so that the gate mechanism assumes the opened condition.

21. The system of claim 20, wherein each gate mechanism is a resiliently deflectable lever having a protrusion normally extending into a respective outlet region.

* * * * *